(12) United States Patent
Marsden

(10) Patent No.: US 7,063,673 B2
(45) Date of Patent: Jun. 20, 2006

(54) COUPLING DEVICE FOR BLOOD COLLECTION ASSEMBLY

(75) Inventor: Stewart Marsden, Montville, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 297 days.

(21) Appl. No.: 10/349,919

(22) Filed: Jan. 23, 2003

(65) Prior Publication Data

US 2004/0147855 A1     Jul. 29, 2004

(51) Int. Cl.
*A61B 5/00*     (2006.01)
*B65D 81/00*    (2006.01)

(52) U.S. Cl. ........................................ 600/576
(58) Field of Classification Search ................ 600/573, 600/576, 577; 604/240–242, 195, 187, 232
See application file for complete search history.

(56) References Cited

U.S. PATENT DOCUMENTS

| | | |
|---|---|---|
| 3,494,352 A | 2/1970 | Russo et al. |
| 4,392,499 A | 7/1983 | Towse |
| 4,449,539 A | 5/1984 | Sarstedt |
| 4,459,997 A | 7/1984 | Sarstedt |
| 4,834,715 A | 5/1989 | Hanifl |
| 4,998,934 A | 3/1991 | Bernstein |
| 5,066,287 A * | 11/1991 | Ryan .................... 604/240 |
| 5,074,312 A | 12/1991 | Sarstedt |
| 5,088,984 A | 2/1992 | Fields |
| 5,174,301 A | 12/1992 | Sarstedt |
| 5,217,025 A | 6/1993 | Okamura |
| 5,607,392 A | 3/1997 | Kanner |
| 5,693,027 A | 12/1997 | Hansen et al. |
| 5,997,275 A | 12/1999 | Sarstedt |
| 6,050,978 A | 4/2000 | Orr et al. |
| 6,183,464 B1 | 2/2001 | Sharp et al. |
| 6,224,568 B1 | 5/2001 | Morimoto et al. |

FOREIGN PATENT DOCUMENTS

| | | |
|---|---|---|
| DE | 196 47 976 A1 | 5/1998 |
| FR | 1 593 629 | 6/1970 |

* cited by examiner

*Primary Examiner*—Max F. Hindenburg
*Assistant Examiner*—Brian Szmal
(74) *Attorney, Agent, or Firm*—Scott Rittman; Mark J. Schildkraut

(57) ABSTRACT

The present invention is directed to a coupler for providing fluid connection between a needle holder and an intravenous needle assembly. The coupler includes a coupler housing and a coupler needle cannula. The coupler housing includes a forward end and a rearward end with the forward end having a piercable septum. The coupler housing also includes at least one lug on its external surface. The coupler is capable of forming a blood collection assembly to provide for fluid connection between a conventional needle holder and an intravenous needle assembly which includes guide slots traditionally provided for engagement with lugs on specific specimen tube arrangements.

20 Claims, 9 Drawing Sheets

COUPLING DEVICE FOR BLOOD COLLECTION ASSEMBLY

BACKGROUND OF THE INVENTION

1. Field of the Invention

The present invention relates to a blood collection assembly. More particularly, the present invention is directed to a coupler for connection of various needle and needle holder configurations.

2. Description of Related Art

Disposable medical devices having medical needles are used for administering medication or withdrawing fluid from the body of a patient. Such disposable medical devices typically include blood-collecting needles, fluid handling needles and assemblies thereof. Current medical practice requires that fluid containers and needle assemblies used in such devices be inexpensive and readily disposable. Consequently, existing blood collection devices typically employ some form of durable, reusable holder on which detachable and disposable medical needles and fluid collection tubes may be mounted. A blood collection device of this nature may be assembled prior to use and then disassembled after use. Thus, these blood collection devices allow repeated use of a relatively expensive holder upon replacement of relatively inexpensive medical needles and/or fluid collection tubes. In addition to reducing the cost of collecting blood specimens, these blood collection devices help minimize the production of hazardous waste material.

One particular example of a blood extraction device is described in U.S. Pat. No. 4,449,539 and sold under the name MONOVETTE™ by Sarstedt. This patent describes a device including a cylindrical extraction tube having a piston therein and a cap on an end thereof, which can be attached with a double-ended needle cannula having an intravenous puncture tip and a non-patient puncture tip with a self-sealing hose or sleeve around the end thereof. The cap of the tube includes a puncturable closure which can be pierced by the non-patient needle when the tube and the double-ended needle cannula are attached. The tube and double-ended needle cannula are attached through lugs on the closure of the tube which engage slots on a skirt of the needle cannula to lock the tube and the needle together for use in sampling. In such an arrangement, however, multiple sampling involves separating the lug and slot engagement between the needle and the tube and attaching a new tube through the lugs and slots.

Moreover, other blood collection tubes and needles made by other manufacturers are not compatible with the lug and slot configuration as described above. For example, the VACUTAINER™ brand of blood collection assemblies sold by Becton, Dickinson and Company includes an evacuated blood collection tube with a piercable stopper which is inserted into a hollow needle holder having a double-ended needle attached thereto. Such collection tubes are not interchangable with the lug and slot arrangement described above. Accordingly, a user of one of these systems for sampling of blood from a patient cannot interchange collection tubes between the systems. To switch to the tube of another manufacturer during sampling of a patient, it is necessary to remove the needle from the patient and re-insert a new needle into the patient, causing discomfort to the patient.

Accordingly, a need exists for a blood collection system in which a plurality of blood collection containers of different manufacturers can be interchanged with a single sampling needle for collection of multiple specimens from a patient or for use of the needle of one manufacturer with the collection containers of another manufacturer.

SUMMARY OF THE INVENTION

The present invention is directed to a coupler which includes a coupler housing and a coupler needle cannula, for providing fluid connection between a needle holder and an intravenous needle assembly for blood collection. The coupler housing includes a forward end and a rearward end, with the forward end including a piercable septum therein. The coupler needle cannula extends from the rearward end of the coupler housing. At least one lug, and preferably a plurality of lugs, are present on an external surface of the coupler housing. Such lugs provide for engagement with corresponding grooves present on an intravenous needle assembly. Desirably, the rearward end of the coupler housing includes means for engagement with a needle holder, such as external threads for engagement with threads on a needle holder.

Thus, in a further embodiment, the present invention is directed to a blood collection assembly including a needle holder and an intravenous needle assembly which are connected through such a coupler, with the intravenous needle assembly including guiding slots for corresponding engagement with the lugs of the coupler.

The present invention is further directed to a sampling container needle holder for engagement with a needle assembly having an intravenous puncture end, a non-patient puncture tip and a guide sleeve housing with at least one slot extending along the housing adjacent the non-patient puncture tip. Such a sampling container needle holder includes a needle holder having a hollow body which is capable of accommodating a plurality of sampling containers therein, and a coupler extending from a forward end of the needle holder for providing fluid connection between the needle holder and the needle assembly. The coupler includes a coupler housing having a forward end with a piercable septum therein and a rearward end with a coupler needle cannula extending therefrom. The forward end of the coupler housing accommodates the non-patient puncture tip of the needle assembly puncturing the piercable septum. The rearward end of the coupler housing is connected with the needle holder, such as through a threaded engagement, with the coupler needle cannula extending into the hollow body of the needle holder. The coupler housing further includes at least one lug on an external surface thereof for engagement with the at least one slot of the guide sleeve housing.

In yet a further embodiment, the present invention is directed to a method for collecting a blood sample with a blood collection assembly having a double-ended needle and a needle holder. The method involves providing a needle assembly having an intravenous puncture tip, a non-patient puncture tip and a guide sleeve housing with at least one slot extending along the housing adjacent the non-patient puncture tip, and providing a needle holder capable of accommodating a plurality of sampling containers therein and including a coupler connected to a forward end thereof. The coupler includes a coupler housing having a forward end with a piercable septum therein, a rearward end having a coupler needle cannula extending into the needle holder and at least one lug on an external surface thereof. The needle holder is attached to the needle assembly through the coupler, with the at least one lug on the coupler housing engaging with the at least one slot of the guide sleeve housing. Further, the non-patient puncture tip of the needle assembly punctures the piercable septum of the coupler housing. Thereafter, blood flow is established through the needle assembly and through the coupler needle cannula for collecting a sample of blood in a sampling container within the needle holder. For example, an evacuated blood collection container may be inserted into the needle holder with a stopper of the evacuated blood container being pierced with the coupler needle cannula, thereby establishing a fluid connection between the interior of the evacuated blood container and the intravenous puncture tip of the needle assembly.

DESCRIPTION OF THE PREFERRED EMBODIMENTS

Figure 1:
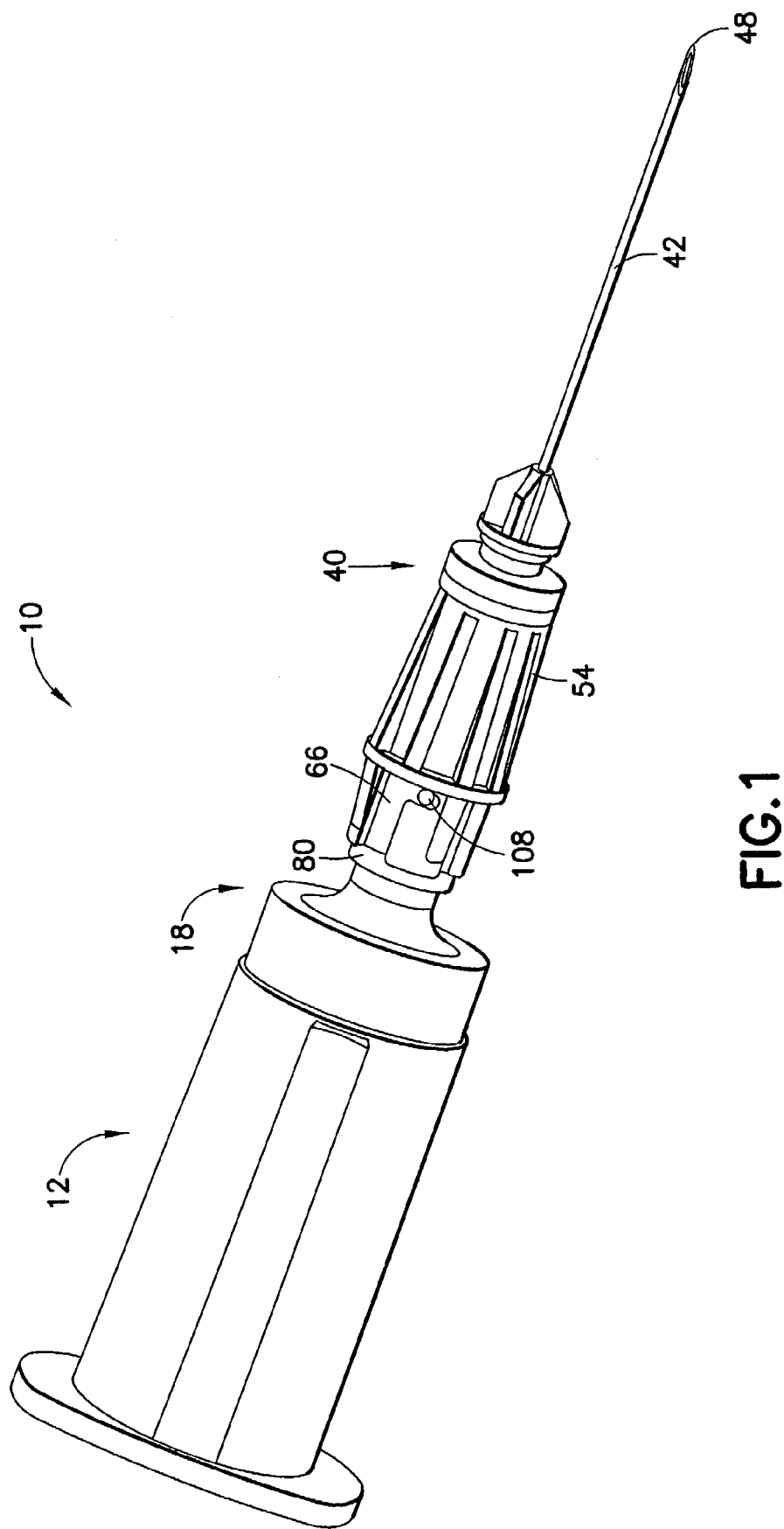
FIG. 1 is a perspective view of a blood collection assembly including a needle holder and an intravenous needle assembly connected through a coupler, in accordance with one embodiment of the present invention.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIG. 1 illustrates a collection assembly including a needle holder and an intravenous needle assembly connected through a coupler, in accordance with the present invention and the related features. The present invention is generally described in terms of a blood collection assembly including a coupler for joining a needle holder with an intravenous needle, and is directed to such an assembly, as well as to the coupler itself and subassemblies incorporating the coupler.

Figure 2:
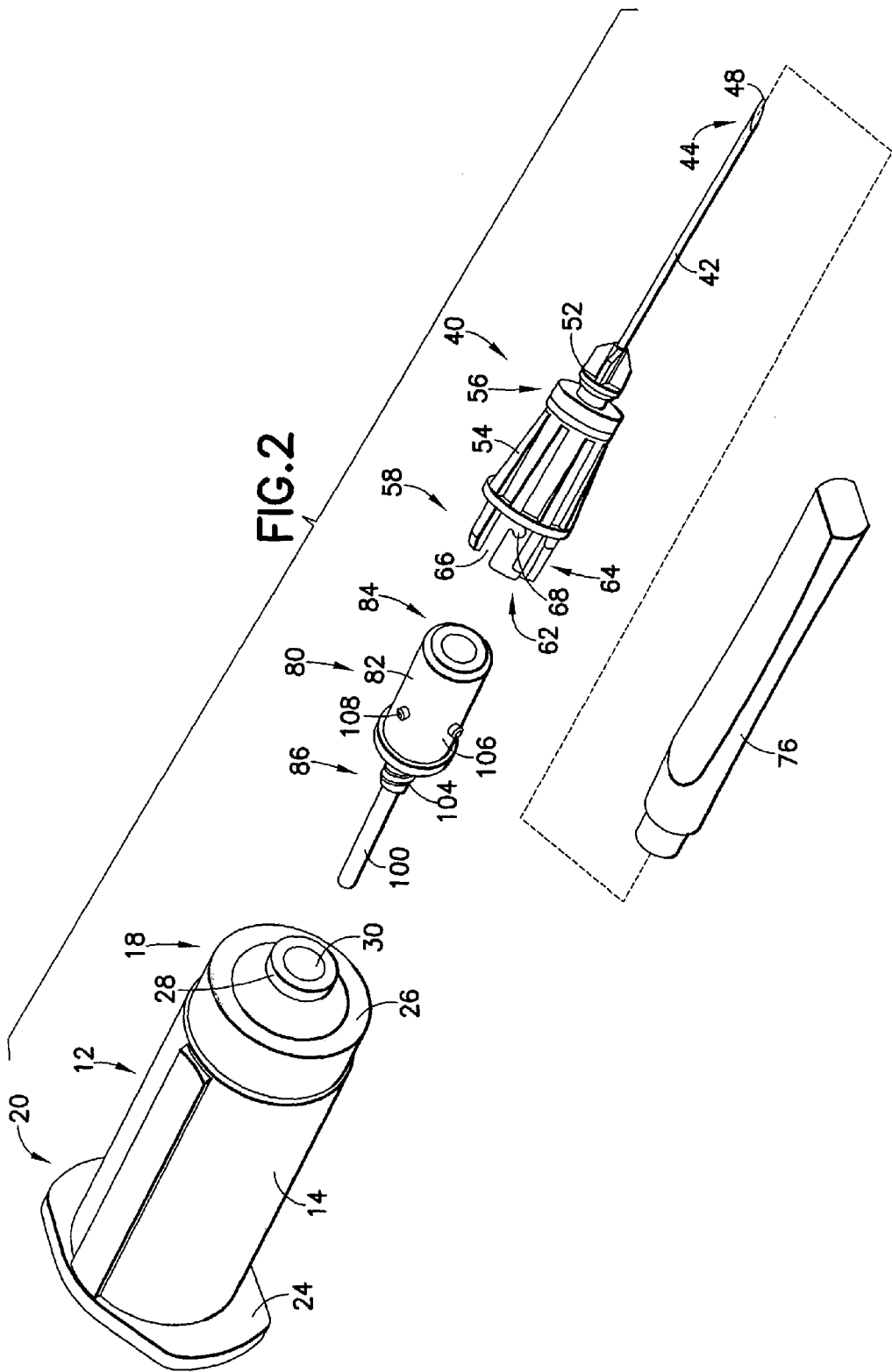
FIG. 2 is an exploded perspective view of the needle holder, the intravenous needle assembly and the coupler of FIG. 1.
Figure 3:
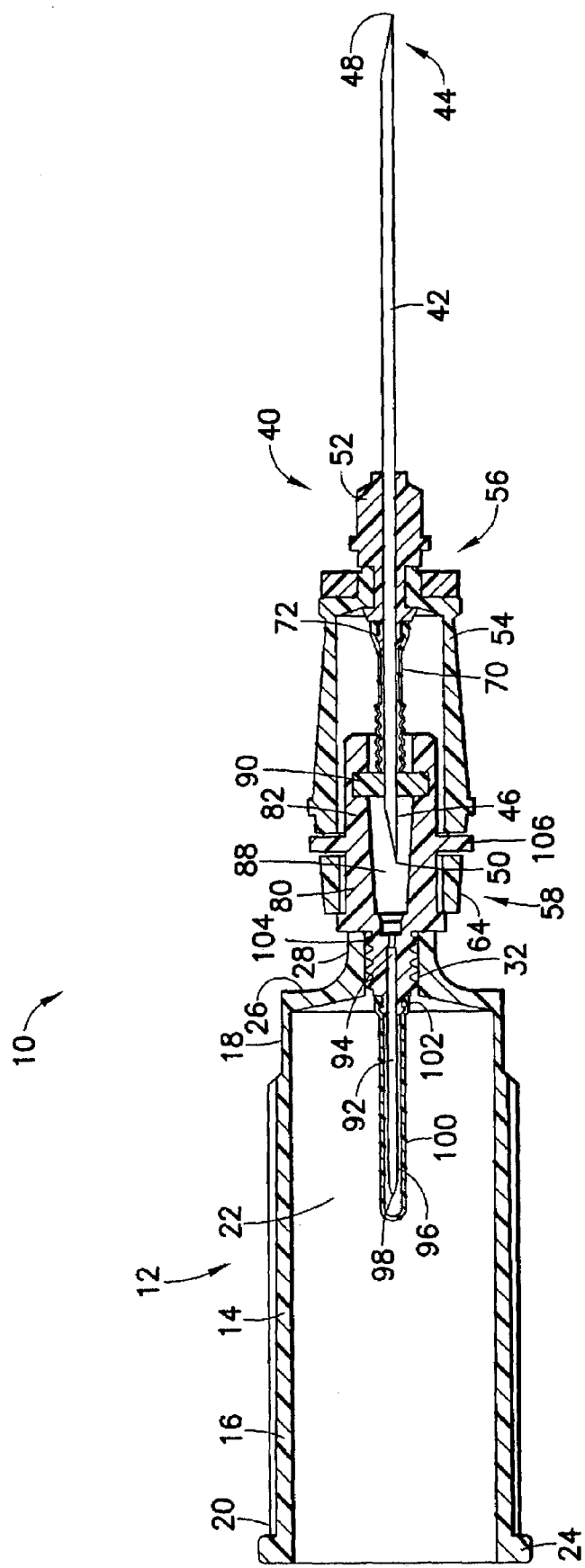
FIG. 3 is a side cross-sectional view of the blood collection assembly of FIG. 1.

FIGS. 1–3 illustrate a blood collection assembly 10 including a needle holder 12 and an intravenous needle assembly 40 which are coupled together through a coupler 80. Needle holder 12 includes a generally tubular or cylindrical housing 14 defined by a tubular wall 16 extending between a forward end 18 and a rearward end 20, with an internal opening 22 extending therethrough. Rearward end 20 of housing 14 is open-ended into an internal opening 22, and may include a flange 24 extending perimetrically outward around the open end at rearward end 20. Internal opening 22 includes an internal diameter which is capable of accommodating blood collection tubes having an outer diameter greater than about 0.4 inches, desirably greater than about 0.62 inches, and more desirably greater than about 0.69 inches. Forward end 18 of housing 14 includes a forward wall 26 which extends to a shoulder to form a cylindrical neck 28. Neck 28 includes an aperture such as an opening 30 therethrough which extends into internal opening 22 of housing 14. Means for engagement with a separate needle assembly to maintain such a needle assembly attached to needle holder 12 during a blood collection procedure is further provided at forward end 18. For example, internal threads 32 may be provided within the opening 30 of neck 28, which are provided for threaded engagement with corresponding threads on a needle assembly. Alternatively, any means for engagement which is capable of connecting a needle assembly to needle holder 12 may be provided, such as a snap-fit engagement, releasable engagement, and other connections.

Needle holder 12 may be constructed of any material known in the art, and is desirably a polymeric material. Desirably, needle holder 12 is constructed of polypropylene. One particular example of a blood collection needle holder which is particularly useful is the VACUTAINER® brand needle holder available from Becton, Dickinson and Company of Franklin Lakes, N.J.

Blood collection assembly 10 also includes intravenous needle assembly 40. Intravenous needle assembly 40 is, generally speaking, a double-ended needle assembly including a guide sleeve having slots for engagement with a top of a collection tube. An example of such a needle assembly is sold in combination with the MONOVETTE™ system by Sarstedt Company of Germany.

Intravenous needle assembly 40 as shown in the present invention includes a hollow needle cannula 42 having a forward intravenous end 44 and a rearward non-patient end 46 with an internal lumen extending therethrough. Intravenous end 44 of needle cannula 42 is beveled to define a sharp puncture tip at intravenous puncture tip 48. Intravenous puncture tip 48 is provided for insertion into a patient's blood vessel, such as a vein, and is therefore designed to provide ease of insertion and minimal discomfort during venipuncture. Non-patient end 46 of needle cannula 42 includes a non-patient puncture tip 50, which includes a sharp puncture tip typically provided for puncturing a stopper or septum of a collection tube during a blood collection procedure. It is contemplated that the forward intravenous end 44 and the rearward non-patient end 46 of needle cannula 42 may be provided as distinct and separate members, so long as fluid flow is established between the two ends.

Needle cannula 42 may be supported by hub 52, which includes an interior opening through which needle cannula 42 extends. Hub 52 is further connected with guide sleeve housing 54. Hub 52 and guide sleeve housing 54 may be separate members which are fixedly adhered, or may be integrally formed as a single member. Guide sleeve housing 54 includes a forward end 56 and a rearward end 58 with a rearward opening 62. Guide sleeve housing 54 further defines a rearward annular skirt 64 at the rearward end 58 thereof. Needle cannula 42 extends through guide sleeve housing 54, with the intravenous end 44 of needle cannula 42 extending from forward end 56 of the guide sleeve housing 54, and with the non-patient end 46 of needle cannula 42 contained within the rearward annular skirt 64 of guide sleeve housing 54. An elastomeric sleeve or sheath 70 may be provided about the non-patient end 46 of needle cannula 42, encompassing non-patient puncture tip 50.

Figure 8:
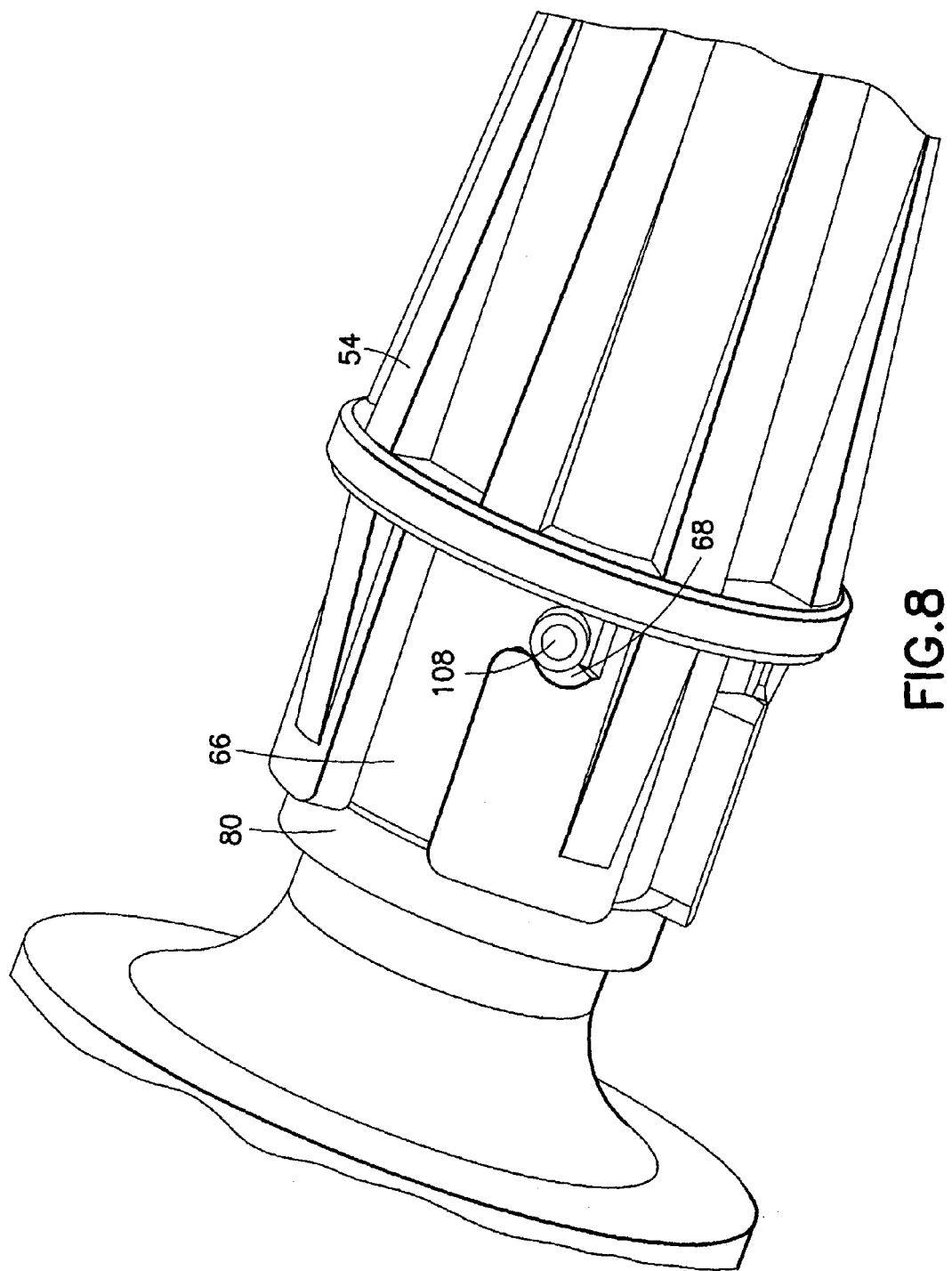
FIG. 8 is an enlarged perspective view showing the connection engagement between the coupler and the intraveneous needle assembly.

The rearward end 58 of the guide sleeve housing 54 further includes axial slots 66 which are distributed around the periphery of the rearward annular skirt 64 of guide sleeve housing 54. Axial slots 66 preferably extend through the thickness of the guide sleeve housing 54 from the rearward end 58 of guide sleeve housing 54 and partially along the longitudinal axis toward the forward end 56 to an end wall where the axial slots 66 merge into lateral enlargements or recesses 68 which effectively represent a continuation of the axial slots 66 in the peripheral direction, as best seen in FIG. 8. A cover 76 as shown in FIG. 2 may be provided for packaging and storage.

As noted above, needle holder 12 and intravenous needle assembly 40 may be conventional assemblies which cannot be traditionally used in combination due to their different mating connections. Blood collection assembly 10 provides an assembly for mating a needle holder 12 with such an intravenous needle assembly 40 through the use of coupler 80.

Figure 4:
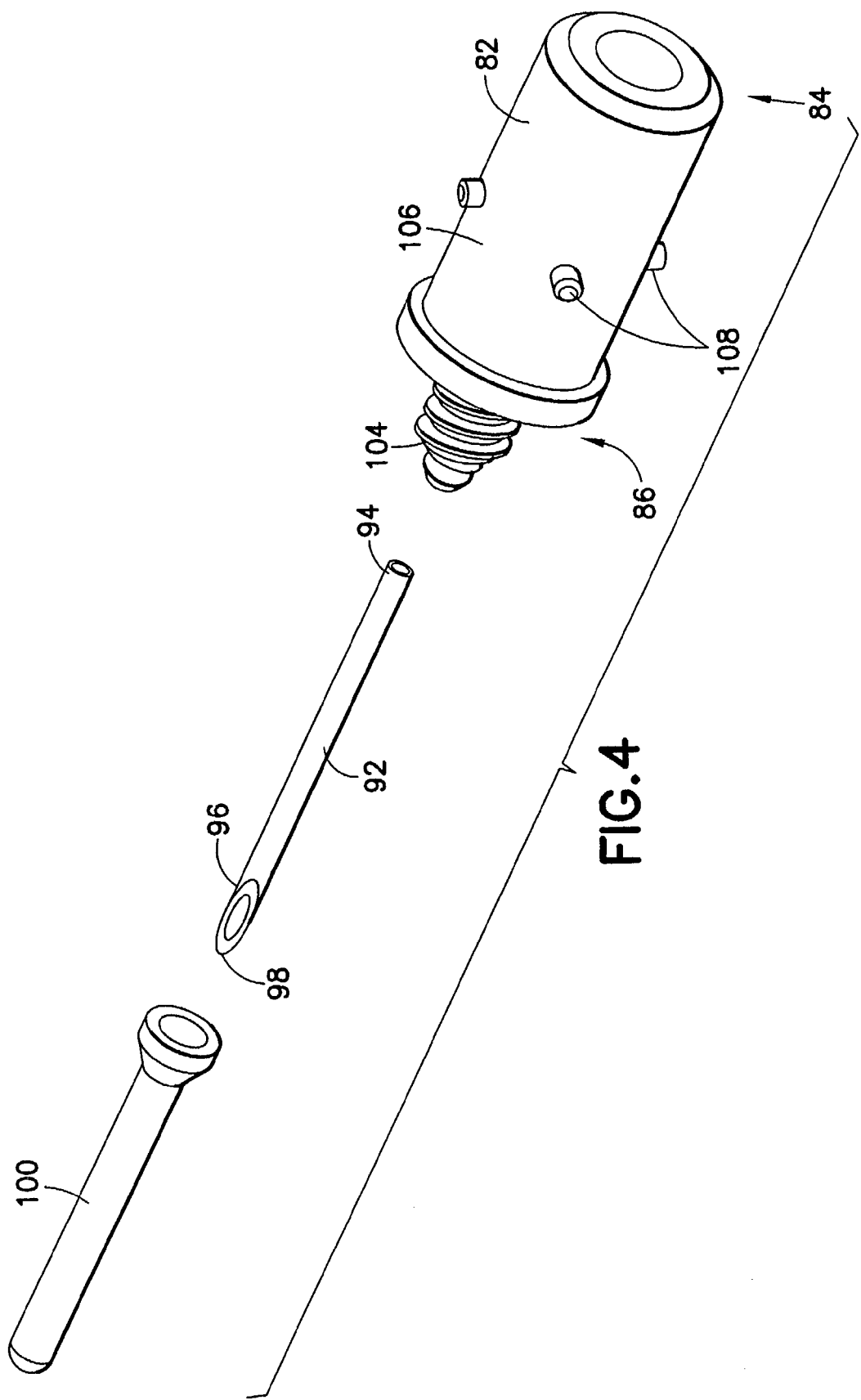
FIG. 4 is an exploded perspective view of a coupler in accordance with the present invention.
Figure 5:
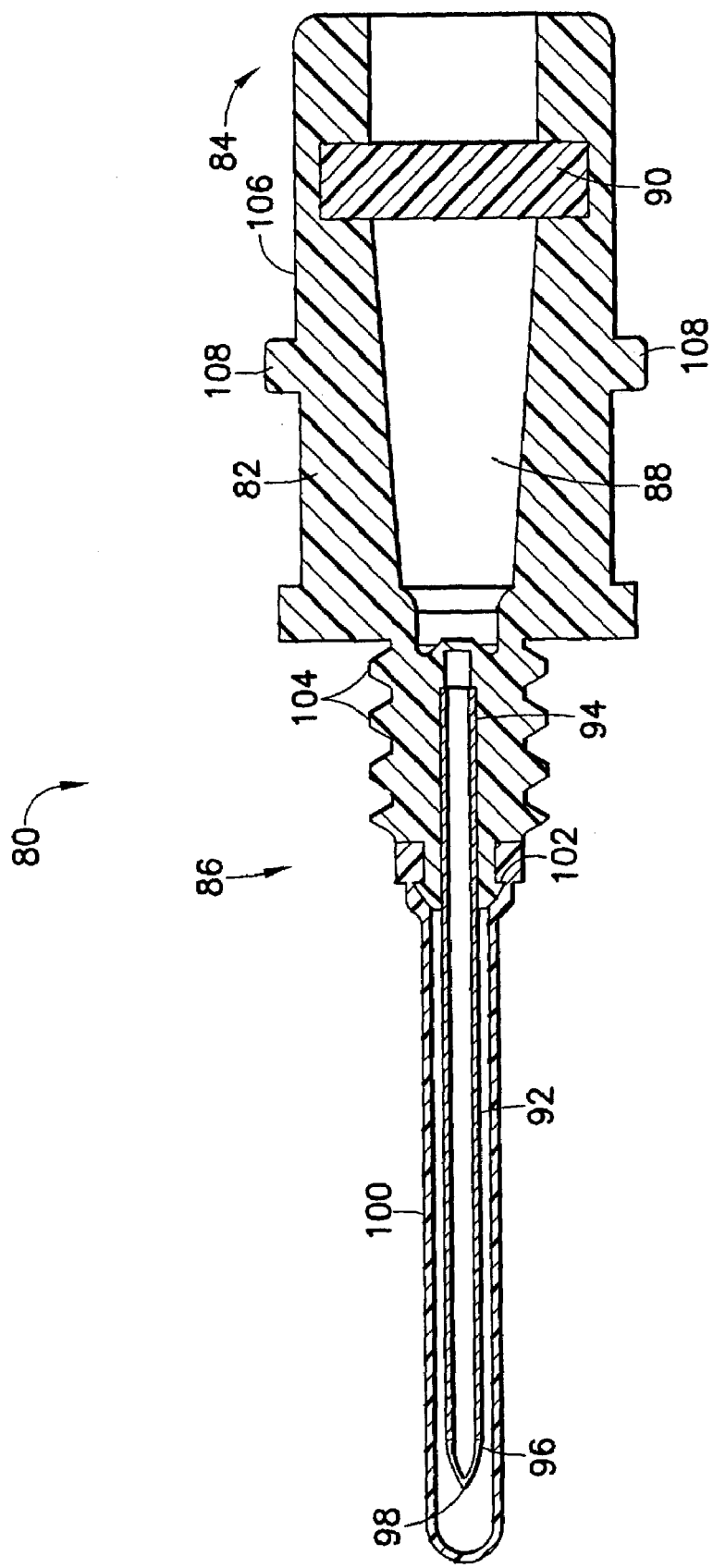
FIG. 5 is an enlarged cross-sectional side view of the coupler of FIG. 4.

As shown in detail in FIGS. 4–5, coupler 80 includes a coupler housing 82 and a coupler needle cannula 92. The coupler housing 82 includes a forward end 84 and a rearward end 86 defining an internal chamber 88 therebetween. A piercable septum 90 is provided within internal chamber 88 at an area adjacent forward end 84. The piercable septum 90 is capable of being punctured by non-patient puncture tip 50 of the intravenous needle assembly 40 to allow fluid connection between the intravenous needle assembly 40, coupler 80 and needle holder 12, as will be described in more detail. Piercable septum 90 can be made of an elastomeric material, such as rubber or the like.

A coupler needle cannula 92 extends from rearward end 86 of coupler housing 82. Coupler needle cannula 92 includes a forward end 94 which extends within and/or is in fluid contact with internal chamber 88 of coupler housing 82, and a rearward end 96, which further defines a non-patient puncture tip 98 in a similar manner as with non-patient puncture tip 50 of intravenous needle assembly 40. An elastomeric sheath 100 may further be provided about the rearward end 96 of coupler needle cannula 92, encompassing non-patient puncture tip 98. A coupler lip 102 may be provided on coupler housing 82 for maintaining such an elastomeric sheath 100 in place.

Figure 9:
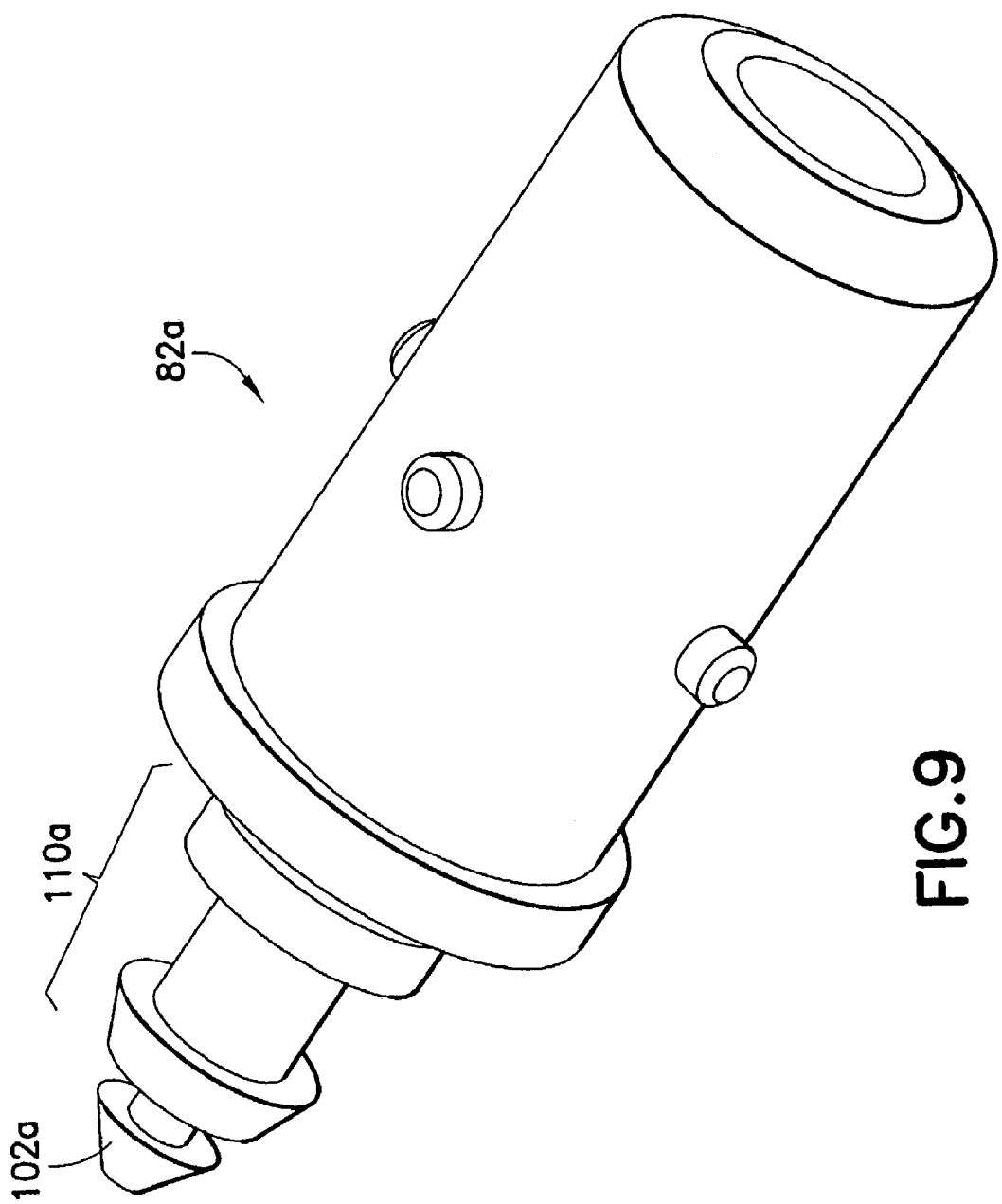
FIG. 9 is a perspective view of a coupler housing in an alternate embodiment of the present invention.

Rearward end 86 of coupler housing 82 is provided with means for engagement with needle holder 12 through opening 30 at forward end 18 thereof. For example, rearward end 86 of coupler housing 82 may include external threads 104 for corresponding threaded engagement with internal threads 32 of needle holder 12. Other means for engagement are also contemplated, such as a snap-fit connection, a releasable connection, and the like. For example, FIG. 9 depicts an alternate coupler housing 82a including a coupler lip 102a for maintaining a sheath as described above, and further including a snap-fit engagement 110a, which provides a profile for snap-fitting within the open end of a needle bolder such as needle holder 12.

As shown in FIGS. 2–5, coupler housing 82 further includes an external surface 106 having at least one lug 108 protruding in a generally radial direction, for corresponding engagement with axial slots 66 of guide sleeve housing 54 of intravenous needle assembly 40. Desirably, the external surface 106 includes a plurality of lugs 108 extending circumferentially about the external surface 106 of coupler housing 82, preferably three lugs, for corresponding engagement with a like amount of axial slots 66.

The coupler housing 82 is desirably constructed of a polymeric material. In one embodiment, coupler housing 82 may be translucent or transparent to define a flashback chamber for allowing a user to visually confirm that a targeted vein has been entered, as is known in the art of blood collection.

Engagement between the coupler 80 and the needle holder 12 is accomplished through means for connecting needle holder 12 and coupler 80, as discussed above. For example, external threads 104 at the rearward end 86 of coupler housing 82 can be threadably engaged within internal threads 32 at the forward end 18 of needle holder 12. In certain embodiments, an adhesive may be used to fixedly adhere the two components together, to form a needle holder assembly including the coupler affixed thereto.

With coupler 80 connected to needle holder 12, the coupler needle cannula 92 extends within the hollow interior of needle holder 12 into the internal opening 22. As such, an evacuated blood collection tube (not shown) inserted within needle holder 12 can be punctured by the non-patient puncture tip 98 of coupler needle cannula 92, with elastomeric sheath 100 being displaced by the front end of a stopper closing the evacuated collection tube in known manner.

Engagement between the coupler 80 and intravenous needle assembly 40 is accomplished through the interengaging structure between axial slots 66 and lugs 108. More particularly, the rearward annular skirt 64 of the guide sleeve housing 54 of intravenous needle assembly 40 is advanced about the external surface 106 at forward end 84 of coupler 80. Each of the lugs 108 are aligned with and introduced into a corresponding axial slot 66 around the periphery of the external surface 106 of the guide sleeve housing 54. An axial guide is established between the guide sleeve housing 54 and the coupler 80. The guide sleeve housing 54 is therefore guided relative to the coupler 80 so that only axial movement is possible. Thus, rotation of the guide sleeve housing 54 and the needle cannula 42 relative to the coupler 80 is no longer possible.

As the guide sleeve housing 54 is advanced further over the forward end 84 of the coupler housing 80, the rearward non-patient end 46 of the needle cannula 42 within intravenous needle assembly 40 makes contact with the piercable septum 90 within coupler housing 82, whereupon elastomeric sheath 70 is displaced by piercable septum 90 and the non-patient puncture tip 50 of the needle cannula 42 penetrates the piercable septum 90. The non-patient end 46 of needle cannula 42 is thus in fluid contact with the internal chamber 88 of coupler 80. Since the forward end 94 of coupler needle cannula 92 also extends within and is in fluid contact with internal chamber 88, fluid flow can be established between needle cannula 42 and coupler needle cannula 92.

The length of the axial slots 66 and the arrangement of the lugs 108 on external surface 106 of coupler 80 are selected such that the lugs 108 are guided in the axial slots 66 up to a position at which the non-patient end 46 of needle cannula 42 has already fully punctured the piercable septum 90 and is located within internal chamber 88 of the coupler 80. When the lugs 108 have reached the front end of the axial slot 66, the guide sleeve housing 54 can be twisted or rotated relative to the coupler 80 so that the lugs 108 enter into the short angled or lateral enlargement or recess 68 and axially lock the guide sleeve housing 54 to the coupler 80.

The cooperating lugs 108 and enlargement or recess 68 thus form a twist actuated locking mechanism between the guide sleeve housing 54 and the coupler 80. The enlargement or recess 68 can be made somewhat wider at its end so that the lugs 108, after entry into the enlargement or recess 68 are secured against unintentional reverse rotation. The enlargement or recess 68 at the end of each axial slot 66 may be inclined rearwardly at an acute angle. The number of axial slots 66 on guide sleeve housing 54 should correspond to the number of lugs 108 on exterior surface 106 of the coupler 80.

In use, each of needle holder 12, intravenous needle assembly 40 and coupler 80 can be provided as separate components separately packaged in a sterile environment, which can be pre-assembled to form a blood collection assembly 10 as shown in FIG. 1.

Figure 6:
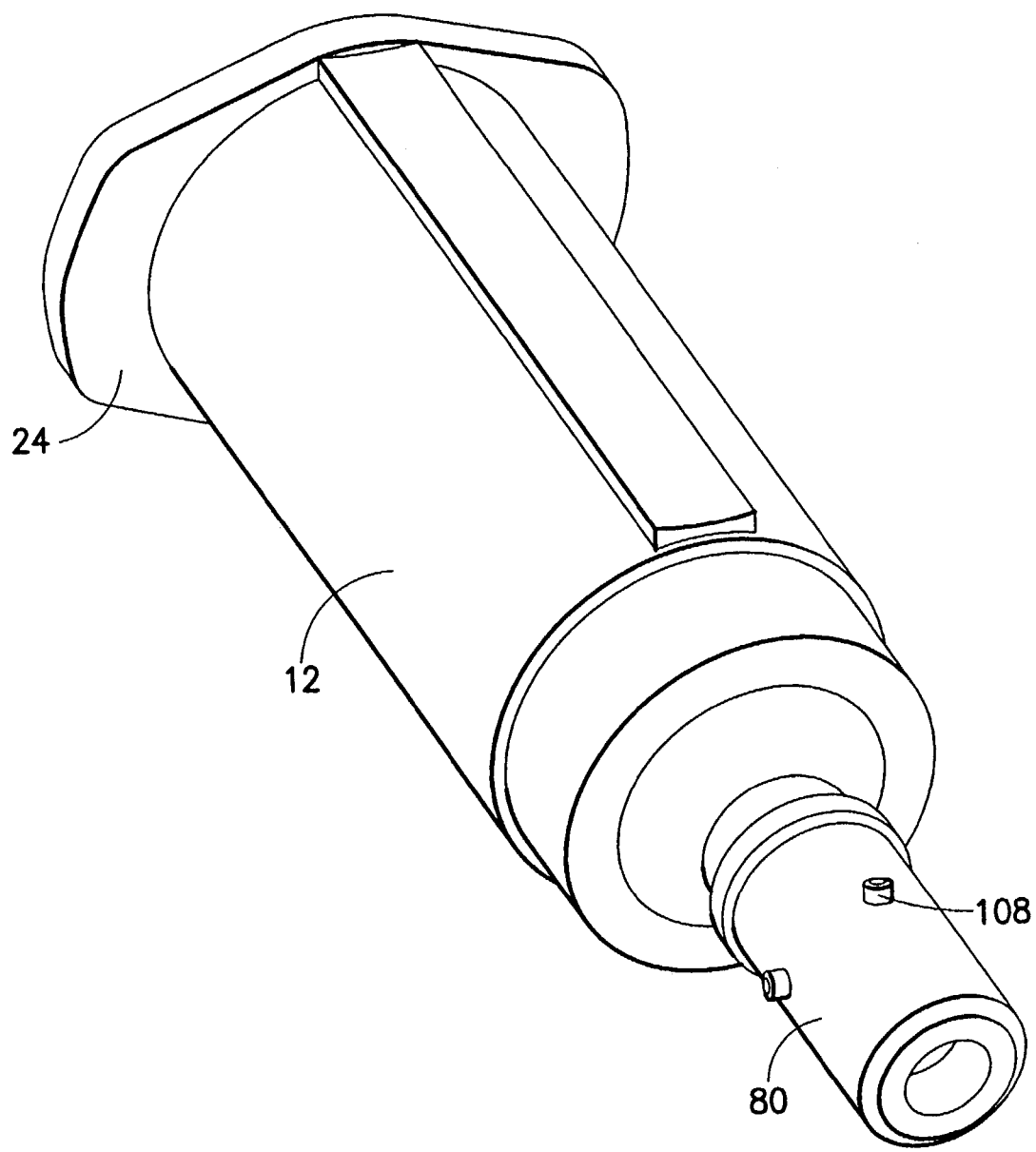
FIG. 6 is a perspective view of a coupler and a needle holder in accordance with a further embodiment of the present invention.
Figure 7:
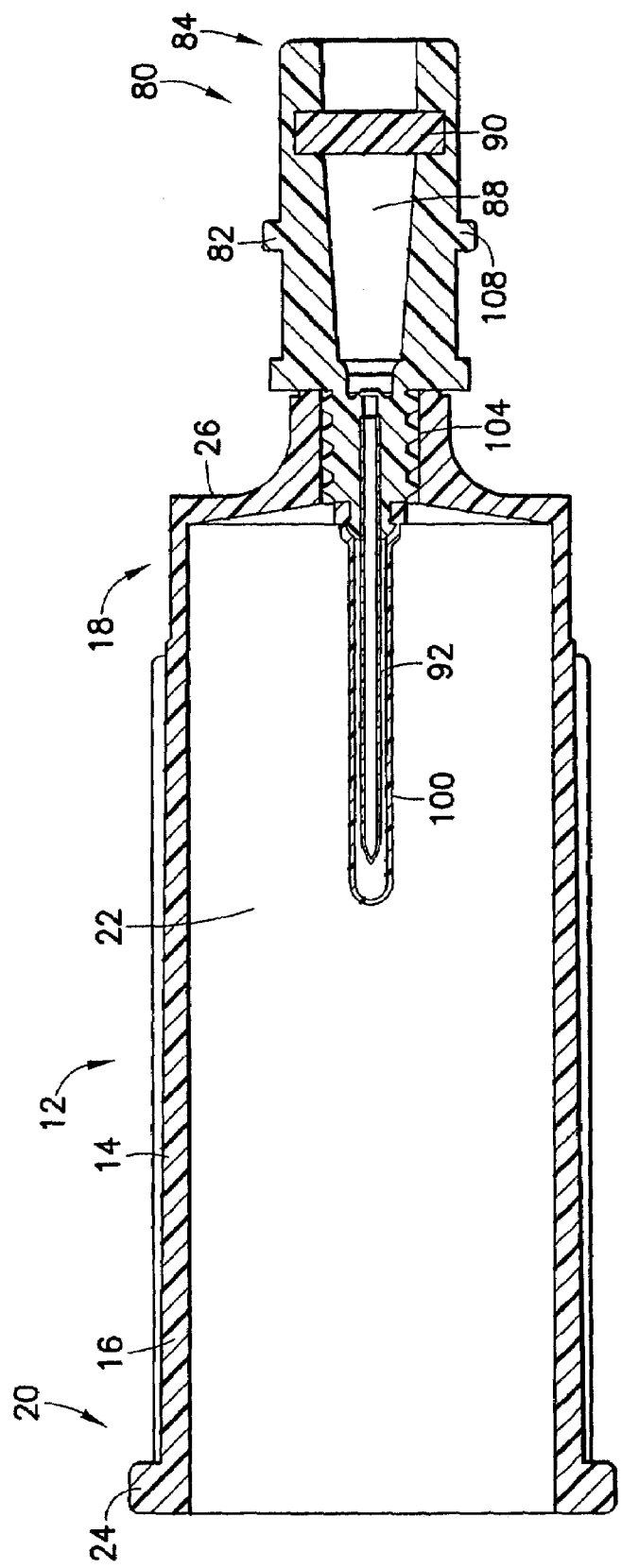
FIG. 7 is a side cross-sectional view of the coupler and the needle holder of FIG. 6.

Alternatively, needle holder 12 and coupler 80 can be provided as a subassembly, as shown in FIGS. 6–7, forming a sampling container needle holder assembly for engagement with a separate intravenous needle assembly 40. In such an embodiment, such a needle holder/coupler subassembly can be connected directly with an intravenous needle assembly 40 before or during use thereof. For example, a phlebotomist may have obtained a blood sample from a patient using a collection system having a collection tube linked with an intravenous needle assembly which includes axial slots such as slots 66 as described above. The phlebotomist may then wish to collect a sample using a different type of collection tube. The phlebotomist can then take the subassembly of the needle holder 12 and coupler 80 as shown in FIGS. 6–7 and attach it directly with the intravenous needle assembly 40 which may still be present in the patient. A collection container such as an evacuated blood collection tube (not shown) can then be inserted within the internal opening 22 of the needle holder 12 and non-patient puncture tip 98 can puncture the stopper of such an evacuated blood collection tube, with the negative pressure within the evacuated tube establishing fluid flow between the intravenous needle assembly 40 and the collection container through coupler 80. As such, the need for withdrawing the needle assembly and re-puncturing the patient with a different needle assembly which is compatible with the desired type of collection tube is avoided.

Moreover, by providing the coupler housing 82 as a single element with both the piercable septum 90 and the coupler needle cannula 92, a single structure can be used to link intravenous needle assembly 40 with a conventional needle holder 12. Such a single element structure of coupler housing 82 therefore eliminates the problems which are apparent with linking together such an intravenous needle assembly 40 and needle holder 12 with a plurality of conventional or "off-the-shelf" adapters, which required interfitting of several pieces in order to provide a direct link between the intravenous needle assembly 40 and needle holder 12.

In a further embodiment, the present invention is directed to a method for collecting blood sample through the use of a blood collection assembly of the type described above, including a double-ended needle and a needle holder. In the method, a needle assembly such as intravenous needle assembly 40 is provided, including an intravenous puncture tip 48, a non-patient puncture tip 50, and a guide sleeve housing 54. The guide sleeve housing includes at least one axial slot 66 extending along the guide sleeve housing 54, as described hereinabove. A needle holder such as needle holder 12 is further provided, which is capable of accommodating a plurality of sampling containers therein, such as for blood collection. The needle holder includes a coupler 80 connected thereto. The coupler includes a piercable septum 90 and a coupler needle cannula 92, as well as lugs 108, as described above. The needle holder 12 is attached to the intravenous needle assembly 40 through the coupler 80, with the lugs 108 of the coupler 80 engaging the corresponding slots 66 of the guide sleeve housing 54, and with the non-patient puncture tip 50 of the intravenous needle assembly 40 puncturing the piercable septum 90 of the coupler 80. Blood flow can then be established through intravenous needle assembly 40 and through coupler needle cannula 92 for collecting a blood sample within a sampling container, as described above.

While the present invention has been described in terms of one embodiment for use in connection with a blood collection system, it is further contemplated that the assembly and the components thereof can be used with other medical procedures known in the art.

The invention claimed is:

1. A coupler for engaging a needle assembly with a needle holder comprising:
   a coupler housing having a forward end and a rearward end, said forward end including a piercable septum therein, said coupler housing including at least one lug on an external surface thereof; and
   a coupler needle cannula extending from said rearward end of said coupler housing;
   wherein the at least one lug is configured to removably engage the coupler with the needle assembly.

2. The coupler according to claim 1, further comprising an elastomeric sheath encompassing the coupler needle cannula which extends from said rearward end of said coupler housing.

3. The coupler according to claim 1, wherein the coupler has a plurality of lugs.

4. The coupler according to claim 3, wherein the coupler has at least three lugs.

5. The coupler according to claim 1, wherein the rearward end of the coupler housing includes means for engagement with a needle holder.

6. The coupler according to claim 1, wherein the rearward end of the coupler housing includes external threads for engagement with a needle holder.

7. The coupler according to claim 6, wherein the rearward end of the coupler housing includes a profile for snap-fit engagement with a needle holder.

8. A blood collection assembly comprising a needle holder and an intravenous needle assembly which are coupled together through the coupler of claim 1, wherein the intravenous needle assembly includes slots for corresponding engagement with said lugs of said coupler.

9. A sampling container needle holder assembly for engagement with a needle assembly having an intravenous puncture end, a non-patient puncture tip and a guide sleeve housing with at least one slot extending along said housing adjacent said non-patient puncture tip, said needle holder assembly comprising:
   a needle holder comprising a hollow body having a forward end and a rearward end having an internal opening, said needle holder capable of accommodating a plurality of sampling containers therein; and
   a coupler extending from said forward end of said needle holder for providing fluid connection between the needle holder and the needle assembly, said coupler comprising a coupler housing having a forward end including a piercable septum therein and a rearward end having a coupler needle cannula extending therefrom, said forward end of said coupler housing accommodating said non-patient puncture tip of said needle assembly puncturing said piercable septum, said rearward end of said coupler housing connected with said needle holder with said coupler needle cannula extending into said hollow body of said needle holder through said forward end thereof, said coupler housing including at least one lug on an external surface thereof for removable engagement with said at least one slot of said guide sleeve housing.

10. The needle holder assembly according to claim 9, further including an elastomeric sleeve extending about said coupler needle cannula.

11. The needle holder assembly according to claim 9, wherein the coupler has a plurality of lugs for engagement with a plurality of corresponding slots on the guide sleeve housing.

12. The needle holder assembly according to claim 9, wherein the coupler housing is transparent and comprises a flash chamber.

13. The needle holder assembly according to claim 9, wherein said connection between said rearward end of said coupler housing and said needle holder comprises a threaded engagement.

14. A method for collecting a blood sample with a blood collection assembly having a double-ended needle and a needle holder, comprising:
   providing a needle assembly having a intravenous puncture tip, a non-patient puncture tip and a guide sleeve housing with at least one slot extending along said housing adjacent said non-patient puncture lip;
   providing a needle holder capable of accommodating a plurality of sampling containers therein and including a coupler connected to a forward end thereof, said coupler comprising
      a coupler housing having a forward end including a piercable septum therein,
      a rearward end having a coupler needle cannula extending into said needle holder
      and at least one lug on an external surface thereof;
   attaching said needle holder to said needle assembly through said coupler with said at least one lug on said coupler housing removably engaging with said at least one slot of said guide sleeve housing and said non-patient puncture tip of said needle assembly puncturing said piercable septum of said coupler housing; and
   establishing fluid flow trough said needle assembly and through said coupler needle cannula for collecting a sample of blood in a sampling container within said needle holder.

15. The method of claim 14, wherein the coupler needle cannula further includes an elastomeric sleeve.

16. The method to claim 14, wherein the coupler includes a plurality of lugs.

17. The method of claim 14, wherein said coupler housing and said needle holder comprise separate members which are connected together.

18. The method of claim 17, wherein said coupler housing and said needle holder are connected through a threaded engagement.

19. The method of claim 14, wherein said needle holder is attached to said needle assembly through said coupler after said intravenous puncture tip of said needle assembly is emplaced within a blood vessel of a patient.

20. The method of claim 14, wherein said fluid flow is established by inserting an evacuated blood collection container into said needle holder and piercing a stopper of said evacuated blood container with said coupler needle cannula, thereby establishing a fluid connection between the interior of said evacuated blood container and said intravenous puncture tip.

* * * * *